US00PP12770P2

(12) United States Plant Patent
Looye

(10) Patent No.: US PP12,770 P2
(45) Date of Patent: Jul. 9, 2002

(54) POINSETTIA PLANT NAMED 'RENATE'

(75) Inventor: Leo Looye, Made (NL)

(73) Assignee: Paul Ecke Ranch, Encinitas, CA (US)

( * ) Notice: Subject to any disclaimer, the term of this patent is extended or adjusted under 35 U.S.C. 154(b) by 20 days.

(21) Appl. No.: 09/779,352

(22) Filed: Feb. 9, 2001

(51) Int. Cl.[7] ..... A01H 5/00
(52) U.S. Cl. ..... Plt./306
(58) Field of Search ..... Plt./306

(56) References Cited

PUBLICATIONS

UPOV–ROM GTITM Computer Database 2001/01, Feb. 6, 2001, GTI Jouve Retrieval Software, Citation for 'Renate'.*

* cited by examiner

*Primary Examiner*—Bruce R. Campell
*Assistant Examiner*—Annette H. Para

(74) *Attorney, Agent, or Firm*—C. A. Whealy

(57) ABSTRACT

A new and distinct cultivar of Poinsettia plant named 'Renate', characterized by its large inflorescences with red purple-colored flower bracts and large cyathia clusters; dark green-colored leaves with burgundy-colored petioles; uniform, upright and outwardly spreading plant habit; very freely branching habit; natural season flower maturity date is December 2 for plants grown in Encinitas, Calif.; response time, about 9.5 weeks; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Renate'.

The new Poinsettia is a naturally-occurring whole plant mutation of the Poinsettia cultivar Peterstar, disclosed in U.S. Plant Pat. No. 8,259. The new Poinsettia was discovered and selected by the Inventor as a single flowering plant within a population of plants of the parent cultivar in a controlled environment in Made, The Netherlands, in December, 1998. The selection of this plant was based on its unique and attractive flower bract colors and good plant form and substance.

Asexual reproduction of the new Poinsettia by terminal cuttings taken at Made, The Netherlands, since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Renate'. These charateristics in combination distinguish 'Renate' as a new and distinct cultivar:

1. Large inflorescences with red purple-colored flower bracts and large cyathia clusters.
2. Dark green-colored leaves with burgundy-colored petioles.
3. Uniform, upright and outwardly spreading plant habit.
4. Very freely branching habit.

5. Natural season flower maturity date is December 2 for plants grown in Encinitas, Calif.; response time, about 9.5 weeks.
6. Excellent post-production longevity.

Plants of the new Poinsettia can be compared to plants of the mutation parent, the cultivar Peterstar. In side-by-side comparisons conducted in Encinitas, Calif., plants of the new Poinsettia differed from plants of the cultivar Peterstar in the following characteristics:

1. Plants of the new Poinsettia are shorter, but more outwardly spreading than plants of the cultivar Peterstar.
2. Plants of the new Poinsettia have smaller leaves than plants of the cultivar Peterstar.
3. Plants of the new Poinsettia have smaller flower bracts, but larger cyathia clusters than plants of the cultivar Peterstar.
4. Flower bract color of plants of the new Poinsettia is red purple whereas flower bract color of plants of the cultivar Peterstar is red.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical plant of 'Renate'.

The photograph at the top of the second sheet comprises a top perspective view of a typical plant of 'Renate'.

The photograph at the bottom of the second sheet is a close-up view of typical leaves and flower bracts of 'Renate' (top) and 'Peterstar' (bottom). Plants used in the photographs were about 18.5 weeks old.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Single plants were grown in 16.5-cm pots, pinched one time, and flowered under naturally lengthening nyctoperiods during the fall. Plants used for the description were about 18.5 weeks old.

In the following description, color references are made to The Royal Horticultural Society Colour Chart except where general terms of ordinary dictionary significance are used.

Botanical classification: *Euphorbia pulcherrima* Willd. cultivar Renate.

Parentage: Naturally-occurring whole plant mutation of *Euphorbia pulcherrima* Willd. cultivar Peterstar, disclosed in U.S. Plant Pat. No. 8,259.

Propagation:

*Type cutting.*—Terminal cuttings.

*Time to initiate roots.*—About 10 days at 20 to 22° C.

*Time to develop roots.*—About 28 days at 20 to 22° C.

*Rooting habit.*—Thick, fibrous and freely-branching.

Plant description:

*Plant form.*—Inverted triangle, top of plant rounded; mounding.

*Growth habit.*—Uniform, upright and outwardly spreading plant habit. Very freely branching; branching is enhanced by removing the shoot apex; about 8 lateral branches develop after removal of the terminal apex. Moderate vigor to vigorous.

*Plant height.*—About 28 cm.

*Plant diameter or spread.*—About 63 cm.

*Crop time.*—From unrooted cuttings to a flowering plant in a 16.5-cm container, about 18.5 weeks are required.

*Stem description.*—Lateral branch length: About 25 cm. Lateral branch diameter: About 1 cm. Internode length: About 2.25 cm. Stem color: 146A.

*Foliage description.*—Alternate, simple. Quantity of leaves per lateral branch: About 10.Length: About 10.5 cm. Width: About 7 cm. Shape: Mostly ovate; occasionally slightly lobed. Apex: Acute. Base: Acute. Margin: Entire. Texture: Mostly glabrous with very slight pubescence on lower surface. Surface: Smooth, not rugose. Color: Young foliage, upper surface: 147A. Young foliage, lower surface: 147B. Mature foliage, upper surface: 147A; venation, 145B. Mature foliage, lower surface: 147B; venation, 145B to 145C. Petiole: Length: About 5.75 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time, about 9.5 weeks; natural season flower maturity date is December 2 for plants grown in Encinitas, Calif.

*Post-production longevity.*—Plants of the new Poinsettia maintain good substance and bract color for about 4 to 6 weeks under interior conditions and for about 8 weeks under greenhouse conditions.

*Quantity of inflorescences.*—One per lateral branch, usually about 8 per plant.

*Inflorescence size.*—Diameter: About 27 cm. Height (depth): About 5.5 cm.

*Flower bracts.*—Quantity of flower bracts per inflorescence: Usually about 20 primary bracts and about 6 smaller secondary bracts per inflorescence. Length, largest bracts: About 13 cm; stalk about 5 cm. Width, largest bracts: About 8.5 cm. Shape: Mostly ovate to nearly oval, occasional shallow lobing. Apex: Acute. Base: Rounded to acute. Margin: Entire. Texture: Glabrous, velvety. Surface: Smooth, very slightly rugose. Orientation: Mostly horizontal. Color: Developing, upper surface: 59A. Developing, lower surface: 59C. Mature, upper surface: 185C to 182A with subsequent development. Mature, lower surface: 185C.

*Cyathia.*—Quantity: Usually about 18 to 20 per corymb. Diameter of cyathia cluster: Large, about 4 by 5 cm. Length: About 1.2 cm. Width: About 8 mm. Shape: Ovate. Color: Immature: 144C. Mature: 144B. Peduncle: Length: About 5 mm. Aspect: Strong, erect. Color: 144C. Stamens: Stamen number: Typically at least 10 per cyathium. Anther shape: Oval. Anther length: About 1 mm. Anther color: 39A. Amount of pollen: Scarce. Pollen color: 13A. Pistils: Pistil number: One per cyathia. Pistil length: About 1 cm. Stigma shape: Tri-lobed, parted. Stigma color: 46A. Style length: About 3 mm. Style color: 46A. Nectary number: One per cyathia. Nectary color: 23A brushed with 26A.

Disease resistance: Resistance to pathogens common to Poinsettia has not been observed on plants grown under commercial conditions.

It is claimed:

1. A new and distinct cultivar of Poinsettia plant named 'Renate', as illustrated and described.

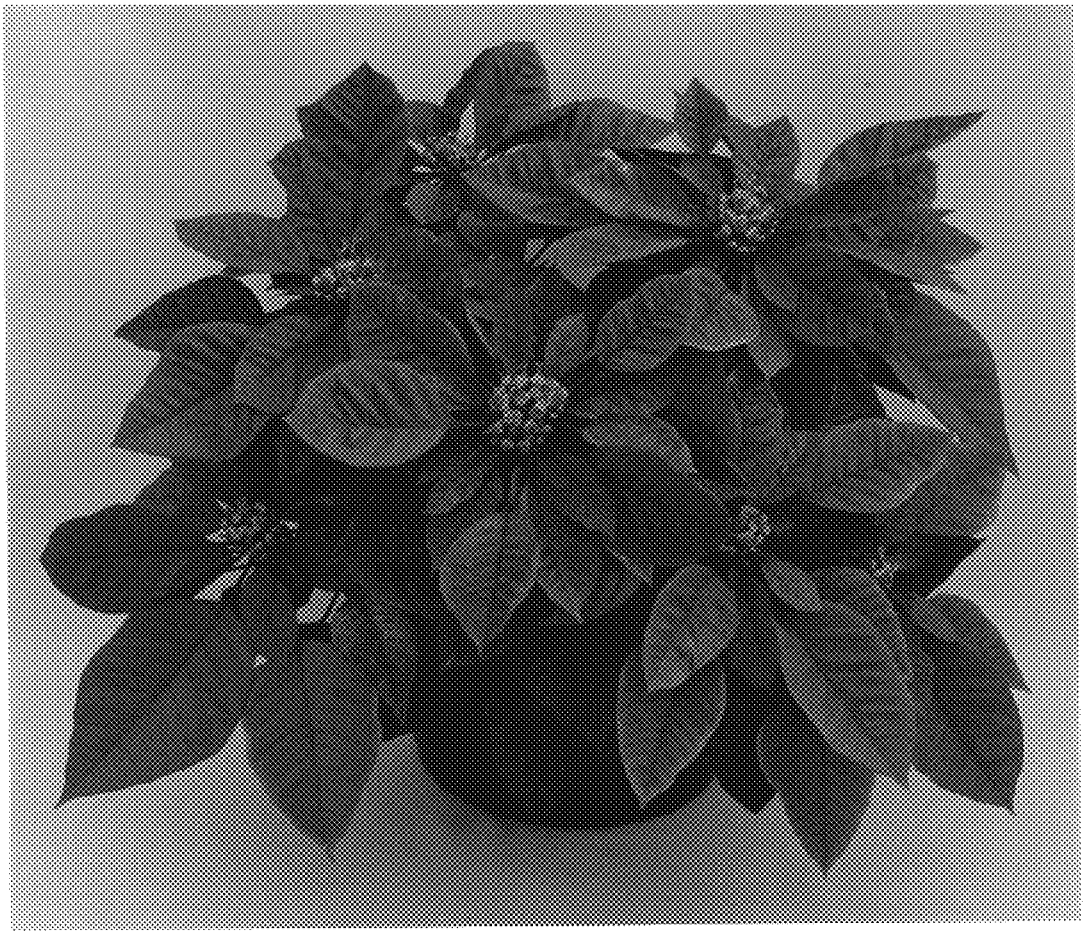

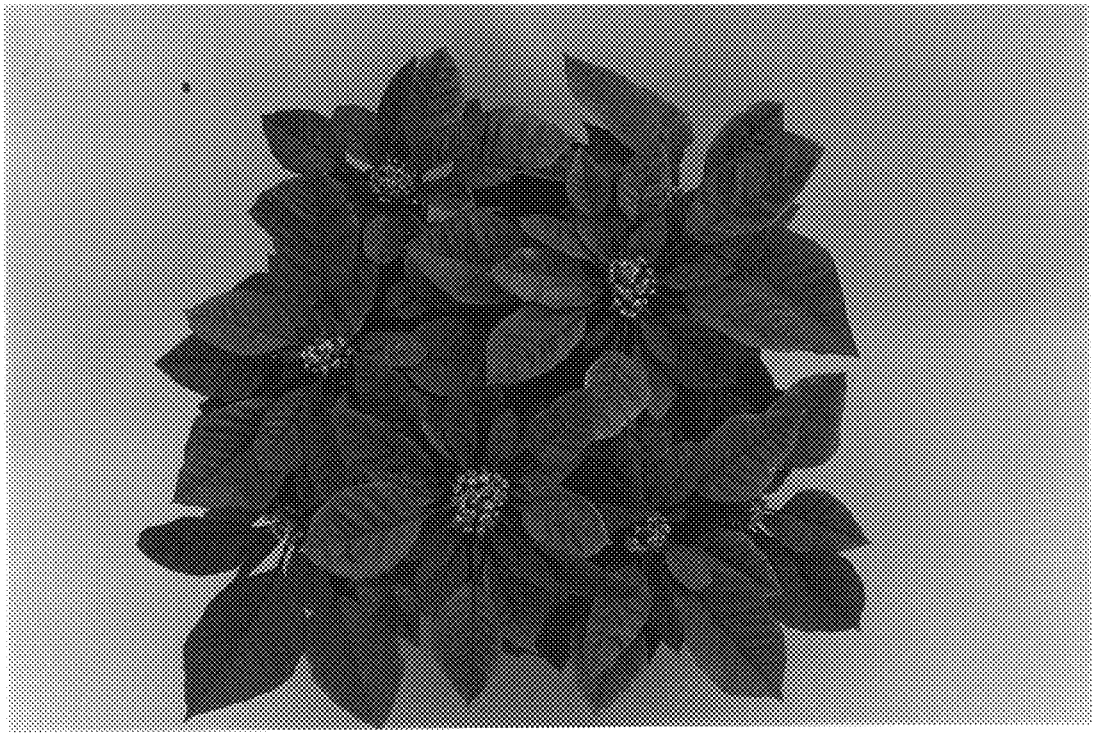
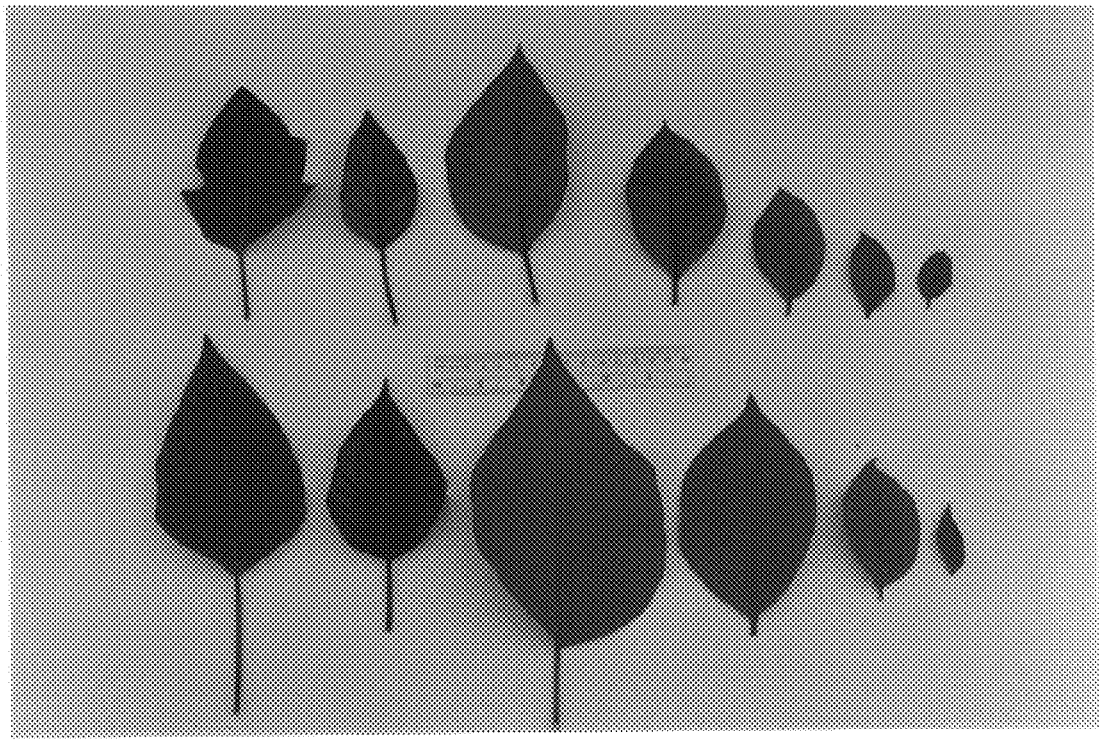

* * * * *